US00PP08995P

United States Patent [19]

Tachibana et al.

[11] Patent Number: Plant 8,995

[45] Date of Patent: Nov. 29, 1994

[54] VERBENA PLANT — 'SUNMAREF TP-R'

[75] Inventors: Ryuichi Tachibana, Yamato; Yuji Tamura, Kofu; Ushio Sakazaki, Hikone, all of Japan

[73] Assignee: Suntory Limited, Osaka, Japan

[21] Appl. No.: 225,079

[22] Filed: Apr. 8, 1994

Related U.S. Application Data

[63] Continuation of Ser. No. 100,148, Aug. 2, 1993, abandoned.

[51] Int. Cl.[5] ..... A01H 5/00

[52] U.S. Cl. ..... Plt./87

[58] Field of Search ..... Plt. 87

*Primary Examiner*—James R. Feyrer

*Attorney, Agent, or Firm*—Burns, Doane, Swecker & Mathis

[57] ABSTRACT

Disclosed herein is a spreading growth habit verbena plant having long stems. The plant has abundant branching and each node in the said branches contacting the ground commonly forming deep-spreading roots. The plant forms many flowers form in ascending spikes with a great profusion of blooms. The flowers exhibit petals having a reddish purple coloration, with a small pale purplish pink eye. The plant is highly resistant to heat, cold, rain, diseases, and pests.

4 Drawing Sheets

This application is a continuation of application Ser. No. 08/100,148, filed Aug. 2, 1993, now abandoned.

BACKGROUND OF THE VARIETY

The present invention relates to a new and distinct variety of one verbena plant from reciprocal crossing of two verbena plants which were selected from crossing 'Rainbowcarpet Brightpurple' (♀) and a wild type of verbena plant (♂) native to Brazil. The 'Rainbowcarpet Brightpurple' parent is botanically known as *Verbena-×hybrida* Voss.

Verbena of the presently commercialized 'Rainbowcarpet' series is a semi-erect growth habit having medium stems, medium branching, and a scant number of flowers in ascending spikes, and has moderate tolerance to heat and cold. Accordingly, this invention was aimed at obtaining a new variety having a spreading growth habit, much branching, many flowers in a spike, high tolerances to heat and cold, and resistances to diseases and pests, which are more excellent than those of said 'Rainbowcarpet' series, and also having a reddish purple flower color.

A crossing of 'Rainbowcarpet Brightpurple' and a wild type of verbena native to Brazil, in the spring of 1988 at the Plant Biotechnology Laboratory, Institute for Fundamental Research of SUNTORY Ltd., residing at 2913-1 Torihara, Hakushu-cho, Kitakoma-gun, Yamanashi-ken, Japan. From this crossing 75 seedlings were obtained in the spring of 1988, then a reciprocal crossing of the 2 seedlings which were selected from obtained 75 seedling as parents was practiced at the same place. From this reciprocal crossing 10 seedlings were obtained in the summer of 1988, from which 2 seedlings were selected, propagated by cutting, and then grown as a trial by flower bedding and potting from the spring of 1989. Only one of the 2 resulting plants was selected. The botanical characteristics of the finally-selected plant were then examined, using a similar varieties, 'Rainbowcarpet Brightpurple' and 'Rainbowcarpet Rose', for comparison, from the spring of 1990. As a result, it was concluded that this verbena plant is distinguishable from any other variety whose existence is known to us, and this new variety of verbena plant was named 'Sunmaref TP-R' (Tapien Redpurple ®).

In the following description, the color-coding is in accordance with The Horticultural Color Chart of The Royal Horticultural Society, London, England (R.H.S. Color Chart), and the Inter-Society Color Council-Nation Bureau of Standards Color Name (ISCC-NBS Color Name). A color chart based on The Japan Color Standard for Horticultural Plants (JHS Color Chart) is also added for reference.

'Rainbowcarpet Brightpurple' used as the female parent in the obtaining of verbena plants used as parents in the breeding this new variety 'Summaref TP-R' is one of the 'Rainbowcarpet' series bred by the TAKII SEED & SEEDLING Corp., Japan. The 'Rainbowcarper' series includes 'Rainbowcarpet Rose', 'Rainbowcarpet White', 'Rainbowcarpet Red', and the like. The main botanical characteristics of 'Rainbowcarpet Brightpurple' are as follows.

Plant:

*Growth habit.*—Semi-erect.
*Plant height.*—25–30 cm.
*Plant extension.*—30–35 cm.
*Blooming period.*—Late April to November.

Stem:

*Diameter.*—2–3 mm.
*Anthocyanin pigmentation.*—Absent.
*Branching.*—Medium.
*Pubescence.*—Few.
*Length of internode.*—35–40 mm.

Leaf:

*Phyllotaxis.*—Opposite.
*Shape of blade.*—Broadly ovate.
*Length.*—20–25 mm.
*Width.*—15–20 mm.
*Depth of incision.*—Deep.
*Color.*—Deep yellow green (R.H.S. 141A, J.H.S. 3706).
*Pubescence.*—Few.

Flower:

*Direction.*—Ascending.
*Outward curvature of petal.*—Slightly curved.
*Diameter.*—10–15 mm.

*Length.*—13–15 mm.
*Color.*—Vivid purple (R.H.S. 82A, J.H.S. 8606).
*Color intensity.*—Absent.
*Overlapping of petals.*—Separate.
*Spike.*—25–30 mm in length; and 30–35 mm in diameter.
*Calyx.*—0.5–1.0 cm.
*Anthocyanin pigmentation of calyx limb.*—Present.
*Peduncle.*—Less than 2 mm in diameter; and 6.0–8.0 cm in length.
*Number of flowers.*—Few (9±2).
*Reproductive organs.*—1 pistil and 5 stamens.
*Physiological and ecological characteristics.*—Moderate resistances to pests and diseases, and moderate tolerances to cold and heat.

The pollen plant used in the obtaining of verbena plants used as parents in the breeding this new variety 'Summaref TP-R' is a wild typs of verbena plant native to South Brazil and this wild type of plant is presently maintained at the Plant Biotechnology Laboratory of SUNTORY Ltd. The main botanical characteristics of the pollen parent are as follows.

Plant:
*Growth habit.*—Spreading.
*Plant height.*—10–15 cm.
*Plant extension.*—80–100 cm.
*Blooming period.*—Late April to November.
Stem:
*Extending.*—40–50 cm.
*Diameter.*—2–3 mm.
*Anthocyanin pigmentation.*—Absent.
*Branching.*—Abundant.
*Pubescence.*—Medium.
*Length of internode.*—20–30 mm.
Leaf:
*Phyllotaxis.*—Opposite.
*Shape of blade.*—Ovate.
*Length.*—15–20 mm.
*Width.*—10–15 mm.
*Depth of incision.*—Deep.
*Color.*—Deep yellow green (R.H.S. 141A, J.H.S. 3706).
*Pubescence.*—Medium.
Flower:
*Direction.*—Ascending.
*Outward curvature of petal.*—Slightly curved.
*Diameter.*—10–15 mm.
*Length.*—12–15 mm.
*Color.*—Brilliant purple (R.H.S. 86C, J.H.S. 8604).
*Color intensity.*-Absent.
*Overlapping of petals.*—Separate.
*Spike.*—30–40 mm in length; and 35–40 mm in diameter.
*Calyx.*—0.5–1.0 cm in length.
*Anthocyanin pigmentation of calyx limb.*—Absent.
*Peduncle.*—1–2 mm in thickness; and 30–50 mm in length.
*Number of flowers.*—Medium (10±2).
*Reproductive organs.*—1 pistil and 5 stamens.
*Physiological and ecological characteristics.*—High resistances to diseases and pests, and high tolerances to heat and cold.

This new variety of verbena plant, 'Sunmaref TP-R' was asexually reproduced by cutting at the aforementioned the Plant Biotechnology Laboratory, Institute for Fundamental Research of SUNTORY Ltd., residing at 2931-1 Torihara, Hakushu-cho, Kitakoma-gun, Yamanashi-ken, Japan, and the homogeneity and stability thereof were confirmed.

SUMMARY OF THE VARIETY

The new variety of verbena plant has a spread growth habit having very long stems and being very low in height, and spreading area of plant is broad, and thus is very different from similar varieties, 'Rainbowcarpet Rose', and 'Rainbowcarpet Brightpurple'. The plant has abundant branching and bears numerous flowers in ascending spikes, and great profusion of blooms which are clearly distinguishable from the similar varieties, 'Rainbowcarpet Rose', and 'Rainbowcarpet Brightpurple', and the whole bush remains in bloom for a considerable period of time, longer than the blooming period of 'Rainbowcarpet Rose'. The length of internode of the new variety is longer than that of similar varieties, and the each node contacting the ground takes deep-spreading roots, and the plant holds steady the ground. The flowers have petals having a reddish purple color with small pale purplish pink eye color. The plant is highly resistants to cold, heat, diseases, and pests.

DESCRIPTION OF THE VARIETY

Figure 1:
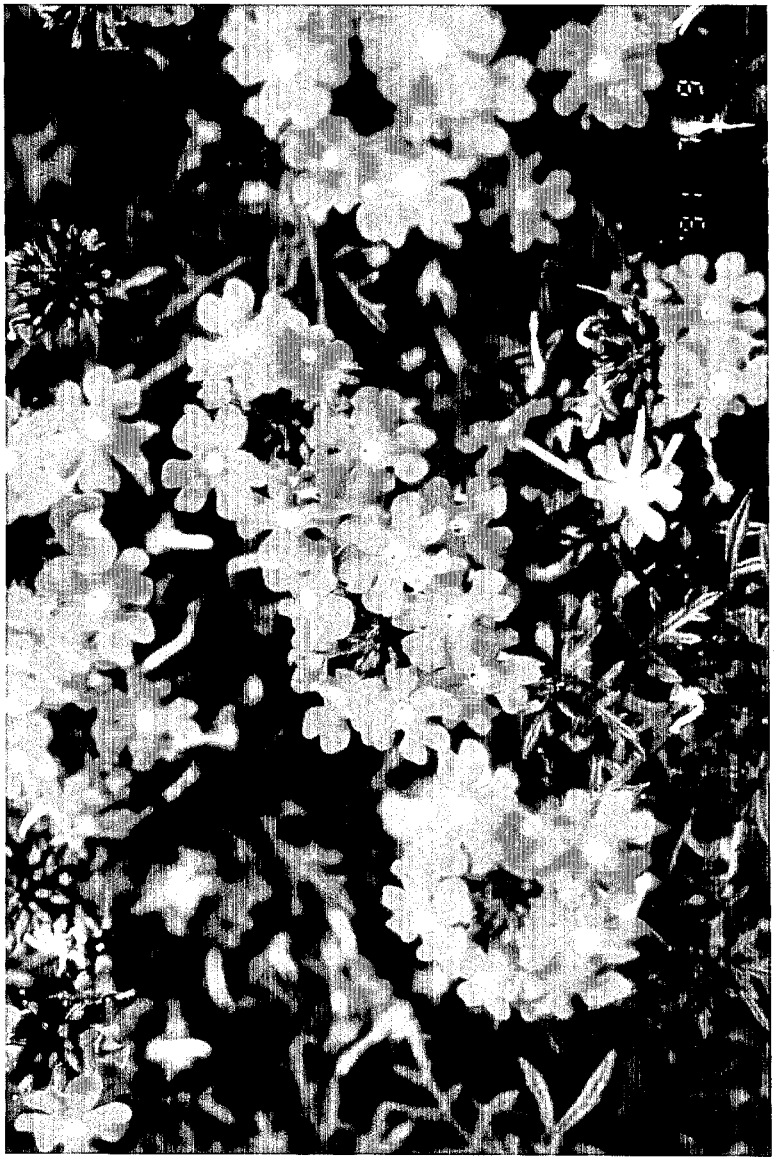
FIG. 1 is photograph of flowers of the new variety of verbena plant.
Figure 2:
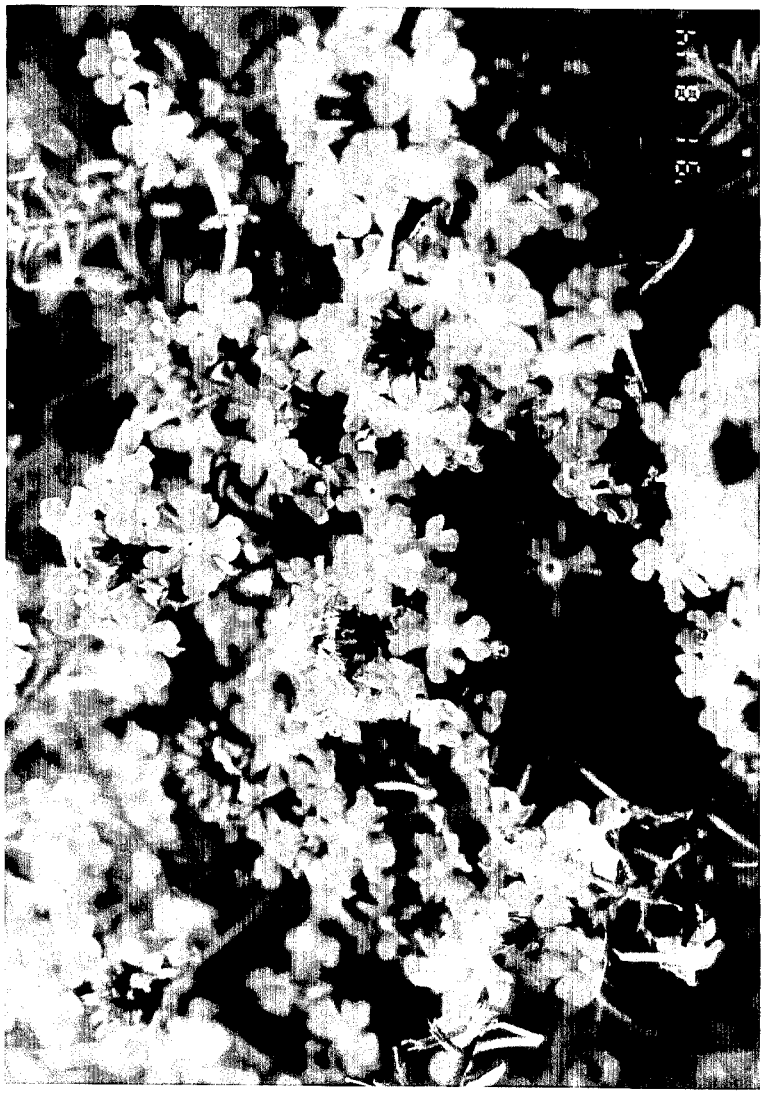
FIG. 2 is a photograph giving a partial view of the new variety of verbena plant planted in a flower bed.
Figure 3:
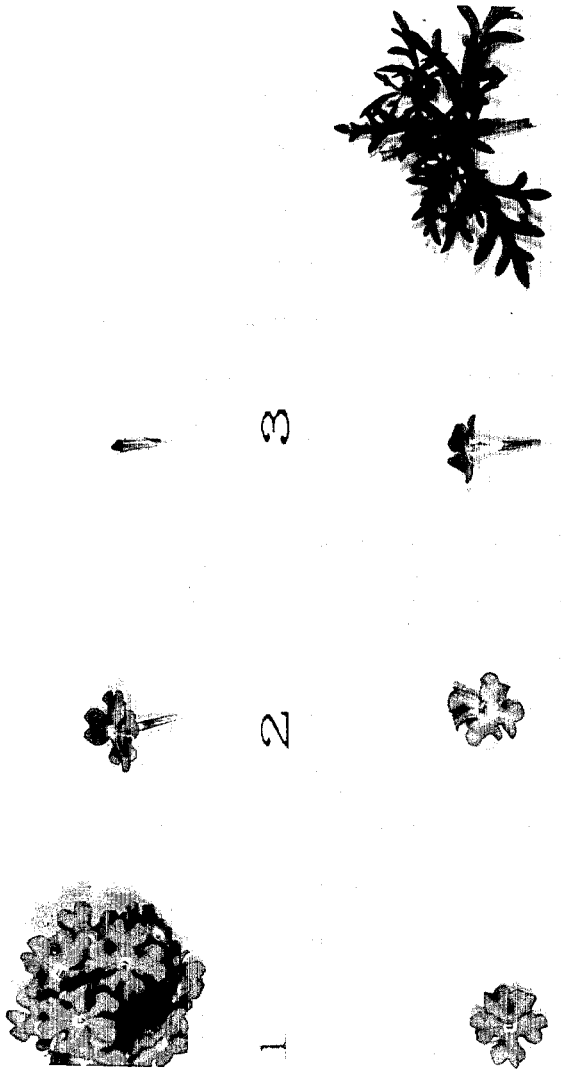
FIG. 3 is a photograph showing, in numerical order, a cluster (1), a flower (2), a bud (3), a surface view of the flower (4), a rear view of the flower (5), a cross-section view of the flower (6), and a branch (7), of the new variety of verbena plant.
Figure 4:
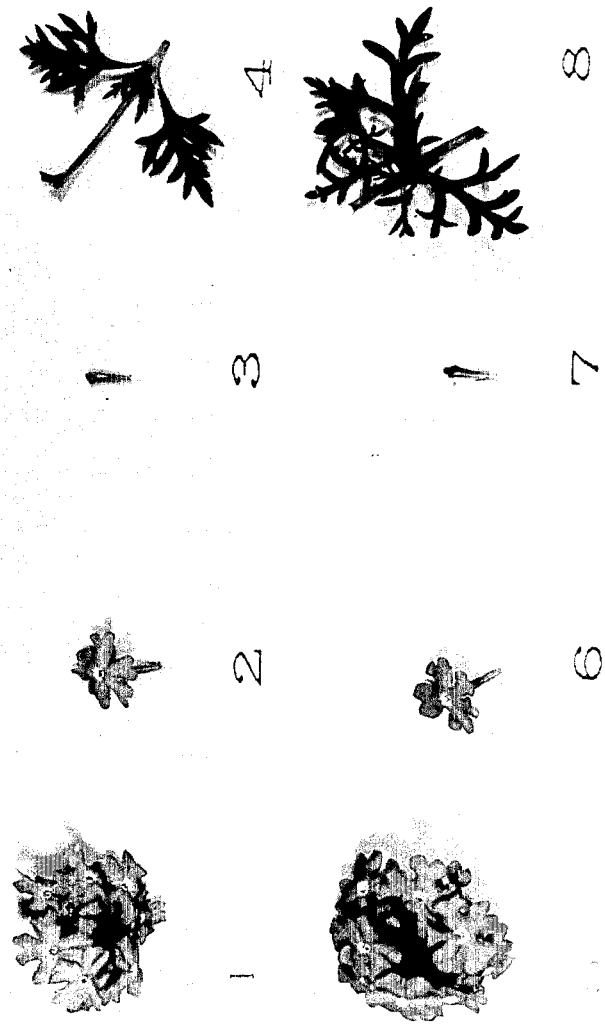
FIG. 4 is a photograph showing, in numerical order, a cluster (1), a flower (2), a bud (3), and a branch (4) of a similar variety 'Rainbowcarpet Brightpurple', in comparison with corresponding items (5–8) of the new variety of verbena plant.

The botanical characteristics of the new and distinct variety of verbena plant, 'Sunmaref TP-R' are as follows.

Plant:
*Growth habit.*—Spread.
*Plant height.*—10–15 cm.
*Spreading area of plant.*—The stem extends to a length of 25–35 cm, with semi-upward portion at the end, and thus the spreading area of the plant is 50–70 cm. After three seasons, the plant commonly spreads to a width of 100 cm., or more.
*Growth.*—Very vigorous with abundant branching and a great profusion of blooms; the whole bush remaining in bloom for a considerable period of time.
*Blooming period.*—Late April to November, in all areas of Japan.
*Ploidy.*—Normal.
Stem:
*Diameter.*-Less than 2 mm.
*Anthocyanin pigmentation.*—Absent.
*Branching.*—Abundant; each node contacting the ground takes deep-spreading roots.
*Length of internode.*—30–50 mm.

*Pubescence.*—Some pubescence commonly is present.

Leaf:

*Phyllotaxis.*—Opposite.

*Shape of blade.*—Progressively cut deeply into the branches in 2 to 3, or more, stages.

*Length.*—25–30 mm.

*Width.*—20–25 mm.

*Depth of incision.*—Deep.

*Color.*—Moderate yellow green (R.H.S. 137C, J.H.S. 3712). Some slight reddish coloration commonly appears during the winter.

*Pubescence.*—Some pubescence commonly is present.

*Stipules.*—Absent.

Flower:

*Direction.*—Upward.

*Outward curvature of petal.*—Slightly curved.

*Diameter.*—14–16 mm.

*Length.*—12–17 mm.

*Cluster.*—Type III; formed from 8 flowers.

*Color.*—Deep reddish purple (R.H.S. 78A, 80A, J.H.S. 8907), with eye color which is pale purplish pink (R.H.S. 761 D, J.H.S. 8920). A conspicuous eye is present where the petals meet the corolla. The coloration may deepen somewhat with age and generally does not fade upon exposure to sunlight.

*Color intensity.*—Absent.

*Overlapping of petals.*—Separate.

*Spike.*—20–30 mm in length; and 35–40 mm in diameter. It is typical for the genies.

*Calyx.*—0.7–1.0 cm in length.

*Anthocyanin pigmentation of calyx limb.*—Generally present in no particular pattern.

*Peduncle.*—Less than 2 mm in thickness; and 2.5–3.0 cm in length.

*Number of flowers.*—Medium (8±2).

*Reproductive organs.*—1 pistil and 5 stamens. Seeds commonly are formed in a very low frequency.

Physiological and ecological characteristics: High tolerances to cold and heat. The new variety is a perennial and has satisfactorily withstood temperatures as low as 0° C. and as high as 35° C. when grown in the field at Osaka, Japan. Also strong resistances to pests and diseases, particularly powdery mildew. The pinching of spent spikes commonly is necessary for a continuation of blossom production. Thinning is not required to maintain the new variety.

This new variety of verbena plant is most suitable for flower bedding and potting, particularly in planters, and is further excellent for ground cover. The new variety grows well in full sun, and has no particular fertilizer requirement for good performance. The plant also grows well in the shade, but commonly does not bloom well in the absence of sunlight. A very strong resistance to mildew is exhibited by the new variety.

The plant of this new variety, 'Sunmaref TP-R' is presently planted and maintained at the Plant Biotechnology Laboratory, Institute for Fundamental Research of SUNTORY Ltd., residing at 2913-1 Torihara, Hakushu-cho, Kitakoma-gun, Yamanashi-ken, Japan.

We claim:

1. A new distinct variety of verbena plant, substantially as herein illustrated and described, characterized particularly as to novelty by (A) a spreading growth habit with long stems, (B) the formation of abundant branching with each node of said spreading branches that contacts the ground commonly forming deep-spreading roots, (C) the formation of many flowers borne on ascending spikes to create a great profusion of blooms, (D) the formation of flowers that have petals having a reddish purple coloration, with a small pale purplish pink eye coloration, and (E) a high resistance to heat, cold, rain, diseases, and pests.

* * * * *